United States Patent
Chao

(10) Patent No.: US 11,077,168 B2
(45) Date of Patent: Aug. 3, 2021

(54) USE OF AN IMMUNOMODULATORY PROTEIN IN REDUCING DAMAGE CAUSED BY FINE PARTICULATE MATTER

(71) Applicant: MYCOMAGIC BIOTECHNOLOGY CO., LTD, New Taipei (TW)

(72) Inventor: Ming Wei Chao, Taoyuan (TW)

(73) Assignee: MYCOMAGIC BIOTECHNOLOGY CO., LTD, New Taipei (TW)

( * ) Notice: Subject to any disclaimer, the term of this patent is extended or adjusted under 35 U.S.C. 154(b) by 0 days.

(21) Appl. No.: 15/944,126

(22) Filed: Apr. 3, 2018

(65) Prior Publication Data

US 2019/0298794 A1  Oct. 3, 2019

(51) Int. Cl.
| | |
|---|---|
| *A61K 38/16* | (2006.01) |
| *A61P 25/28* | (2006.01) |
| *A61K 9/00* | (2006.01) |
| *C07K 14/375* | (2006.01) |

(52) U.S. Cl.
CPC ............ *A61K 38/16* (2013.01); *A61K 9/0053* (2013.01); *A61P 25/28* (2018.01); *C07K 14/375* (2013.01)

(58) Field of Classification Search
CPC ...... A61K 38/16; A61K 9/0053; A61K 38/08; A61K 38/168; A61P 25/28; A61P 25/00; A61P 25/18; C07K 14/375
See application file for complete search history.

(56) References Cited

U.S. PATENT DOCUMENTS

| 7,601,808 B2 | 10/2009 | Lin |
| 2008/0038288 A1 | 2/2008 | Chung et al. |
| 2010/0009915 A1 | 1/2010 | Ko |
| 2016/0115208 A1 | 4/2016 | Chao |

FOREIGN PATENT DOCUMENTS

| CN | 101204406 A | 6/2008 |
| TW | 201625286 A | 7/2016 |
| TW | 201717978 A | 6/2017 |

OTHER PUBLICATIONS

Vickers. A vaccine against Alzheimer's disease: developments to date. Drugs Aging 2002; 19(7):487-94.*
Perrin et al. Multimodal techniques for diagnosis and prognosis of Alzheimer's disease. Nature Oct. 15, 2009;461(7266):916-22, Published online Oct. 14, 2009.*
Hampel et al. The future of Alzheimer's disease: the next 10 years. Prog Neurobiol. Dec. 2011;95(4):718-28. Epub Nov. 22, 2011.*
Puzzo et al. Behavioral assays with mouse models of Alzheimer's disease: practical considerations and guidelines. Biochem Pharmacol. Apr. 15, 2014;88(4):450-67. Epub Jan. 21, 2014.*
Oertel, WH. Recent advances in treating Parkinson's disease. F1000Res. Mar. 13, 2017;6:260. doi: 10.12688/f1000research.10100.1. eCollection 2017.*
Insel, TR. Rethinking schizophrenia. Nature. Nov. 11, 2010;468(7321):187-93. doi: 10.1038/nature09552.*
Button et al. Power failure: why small sample size undermines the reliability of neuroscience. Nat Rev Neurosci. May 2013;14(5):365-76. doi: 10.1038/nrn3475. Epub Apr. 10, 2013.*
D'Hooge, R; De Deyn, PP (Aug. 2001), "Applications of the Morris water maze in the study of learning and memory". Brain Research Reviews 36 (1): 60-90.
Office Action in Taiwan Counterpart Application No. 108110939, dated Apr. 30, 2020, in 6 pages; English translation provided.
Kino, et al.,, "Isolation and Characterization of a New Immunomodulatory Protein, Ling Zhi-8 (LZ-8), from Ganoderma lucidiu", The Journal of Biological Chemistry, vol. 264, No. 1, Issue of Jan. 5, pp. 472-478, 1989.

* cited by examiner

*Primary Examiner* — Gregory S Emch
(74) *Attorney, Agent, or Firm* — Duane Morris LLP

(57) ABSTRACT

The present invention relates to a new use of an immunomodulatory protein derived from *Ganoderma* or a recombinant or a composition thereof in reducing damage caused by fine particulate matter on embryos and offspring. Accordingly, the present invention suggests that the *Ganoderma* immunomodulatory protein administrated to pregnant animals can prevent neurological damages and reduce risk of disorders in embryos and offspring.

8 Claims, 5 Drawing Sheets

Specification includes a Sequence Listing.

USE OF AN IMMUNOMODULATORY PROTEIN IN REDUCING DAMAGE CAUSED BY FINE PARTICULATE MATTER

SEQUENCE LISTING

The instant application contains a Sequence Listing which has been submitted electronically in ASCII format and is hereby incorporated by reference in its entirety. Said ASCII copy, created on Jul. 7, 2020, is named G4590-03000_SL.txt and is 3,152 bytes in size.

FIELD OF THE INVENTION

The present invention relates to a new use of an immunomodulatory protein derived from *Ganoderma* or a recombinant or a composition thereof in reducing damage caused by fine particulate matter on embryos and offspring. Particularly, the immunomodulatory protein is derived from *Ganoderma microsporum*.

BACKGROUND OF THE INVENTION

Air pollution has also become a common concern. One component air pollution, fine particulate matter less than 2.5 μm in diameter, has carbon as the core and adsorbs organic matter, heavy metals and other substances. Fine particulate matter can reach the bronchi through respiration, and enter the body through the bloodstream to affect the whole body via blood circulation. When air pollutants enter a pregnant woman's body, her child will also be affected. It has been reported that congenital heart disease, miscarriage, premature birth and low birth weight may result from exposure to fine suspended particles during pregnancy. The generational central nervous system may also be affected by exposure to fine aerosols during pregnancy.

Many therapeutic effects of Lingzhi species have been reported, such as immunomodulatory, anti-tumor, hepatoprotective, antioxidant, and cholesterol-lowering effects. US 20100009915 provides a method for suppressing proliferation of a cancer cell and a method for suppressing tumor cell mobility, comprising providing to the tumor cell a purified polypeptide of a fungal immunomodulatory protein, LZ-8. U.S. Pat. No. 7,601,808 discloses an immunomodulatory protein cloned from *Ganoderma microsporum* that has immunomodulator efficacy. But these references are irrelevant to immunomodulatory proteins from *Ganoderma* on the reduction of damage by fine particulate matter to humans. TW 201717978 discloses uses of an effective dose of *Ganoderma* extracts for inhibition or reduction of PM2.5-caused toxicity. However, this reference is silent on the immunomodulatory proteins from *Ganoderma*.

SUMMARY OF THE INVENTION

The invention found that an immunomodulatory protein from *Ganoderma* can cross the placental barrier and reduce damage caused by fine particulate matter on embryos and offspring, suggesting that the *Ganoderma* immunomodulatory protein administrated to pregnant animals can prevent neurological damages and reduce risk of disorders in embryos and offspring.

The present invention provides a method for reducing neurological damage to or risk of suffering neurological diseases in embryos or offspring, comprising administering an effective amount of an immunomodulatory protein derived from *Ganoderma*, or a recombinant or a composition thereof, to a pregnant subject exposed in particulate matter.

The present invention also provides a method for enhancing cognition in embryos or offspring, comprising administering an effective amount of an immunomodulatory protein derived from *Ganoderma*, or a recombinant or a composition thereof, to a pregnant subject exposed to particulate matter.

An embodiment of neurological damage is cognitive damage. Certain embodiments of cognition include memory function, long-term memory, short-term memory, working memory and spatial cognition. Certain embodiments of neurological disease include a neurodegenerative disease, schizophrenia or autism disorder.

Certain embodiments of the immunomodulatory protein of *Ganoderma* or a recombinant thereof include an amino acid sequence selected from the group consisting of (1) -Leu-Ala-Trp-Asn-Val-Lys-(LAWNVK; SEQ ID NO:1), (2) -Asp-Leu-Gly-Val-Arg-Pro-Ser-Tyr-Ala-Val- (DLGVRPSYAV; SEQ ID NO:2), (3) the amino acid sequence of: MSDTALIFTLAWNVKQLAFDYTPNWGR-GRPSSFIDTVTFPTVLTDKAYTY RVVVSGKDLGVRPSYAVESDGSQKINFLEYNSGY-GIADTNTIQVYVIDPD TGNNFIVAQWN (SEQ ID NO: 3) and (4) the amino acid sequence of EAEAEFMSDTA-LIFTLAWNVKQLAFDYTPNWGRGRPSS-FIDTVTFPTVLT DKAY-TYRVVVSGKDLGVRPSYAVESDGSQKINFLEYNSGY GIADTNTIQV YVIDPDTGNNFIVAQWNYLEQKLI-SEEDLNSAVDHHHHHH (SEQ ID NO: 4).

Certain embodiments of the immunomodulatory protein of *Ganoderma* or a recombinant thereof include an amino acid sequence selected from the group consisting of:

(1) Leu-Ala-Trp-Asp-Val-Lys-(LAWDVK) (SEQ ID NO: 5) and (2) Asn-Leu-Gly-Val-Lys-Pro-Ser-Tyr-Ala-Val- (NLGVKPSYAV) (SEQ ID NO: 6).

Certain embodiments of the effective amount of the immunomodulatory protein is from about 0.01 mg/kg to about 5 mg/kg.

DETAILED DESCRIPTION OF THE INVENTION

Figure 1A:
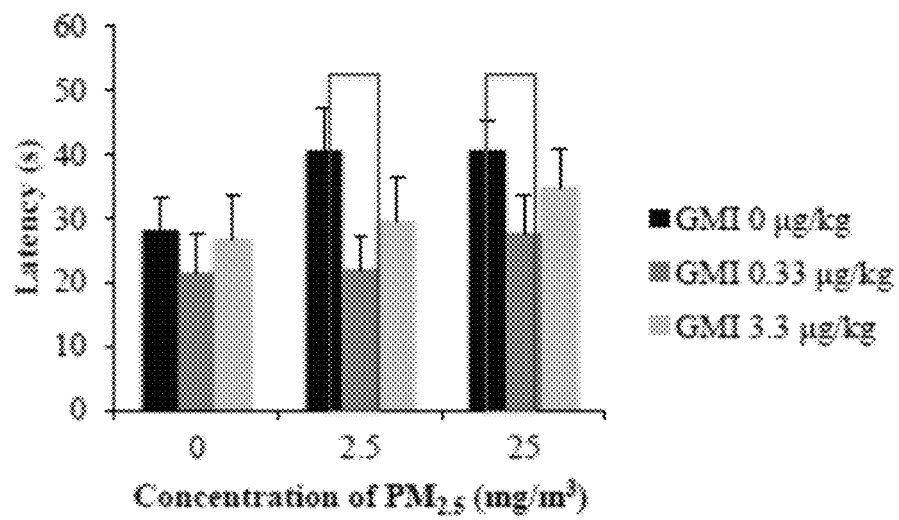
FIGS. 1 (*a*) and (*b*) show that GMI can enhance the long-term memory of offspring. (a) The offspring of pregnant rats received a high dose of PM2.5 spent a longer time exploring the platform, while those that received GMI took less time. (b) The hot spots show that the offspring of pregnant rats that received $PM_{2.5}$ swam around the box, whereas the offspring of pregnant rats that received GMI had higher frequency of swimming at the quadrant with platform.

The invention surprisingly found that an immunomodulatory protein from *Ganoderma* can cross the placental barrier and reduce damage caused by fine particulate matter to embryos and offspring, suggesting that administering the *Ganoderma* immunomodulatory protein to pregnant animals can prevent neurological damage and reduce risk of disorders in embryos and offspring.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

In this application, the use of the singular includes the plural, the article "a" or "an" means "at least one", and the use of "or" means "and/or", unless specifically stated otherwise.

In this application, the word "comprise," or variations such as "comprises" or "comprising," indicate the inclusion of any recited integer or group of integers but not the exclusion of any other integer or group of integers in the specified method, structure, or composition.

As used herein, the term "placental barrier" refers to a semipermeable membrane made up of placental tissues and limiting the kind and amount of material exchanged between mother and fetus.

As used herein, the term "neuron" includes a neuron and a portion or portions thereof (e.g., the neuron cell body, an axon, or a dendrite). The term "neuron" denotes nervous system cells that include a central cell body or soma and two types of extensions or projections: dendrites, by which, in general, the majority of neuronal signals are conveyed to the cell body, and axons, by which, in general, the majority of neuronal signals are conveyed from the cell body to effector cells, such as target neurons or muscle.

As used herein, the term "neurite" encompasses all such cell processes (including both axon and dendrite) growing out of a neuron.

As used herein, the term "neurite outgrowth" refers to the process of cells growing out of a neuron, or to the cells comprising an outgrowth from a neuron.

As used herein, "neurological disorders" means any physiological dysfunction or death of neurons present in the central nervous system or peripheral nervous system or caused by glia cell dysfunction. A non-limited list of such disorders comprises multiple sclerosis, sciatic nerve defect, brain or code injury, dementia, frontotemporal lobe dementia, Alzheimer's disease, Parkinson's disease, Huntington's disease, prion diseases, neuronopathies and motor neuron disorders. "Neuronopathies" are characterized by neuronal cell death of motor neurons or sensory neurons, and hence neuronopathies can be subdivided into motor and sensory neuron disorders.

As used herein, "promote" or "increase", or "promoting" or "increasing" are used interchangeably herein. These terms refer to the increase in a measured parameter in a treated cell (tissue or subject) in comparison to an untreated cell (tissue or subject). A comparison can also be made of the same cell or tissue or subject before and after treatment. In some embodiments, the increase in the treated cell is at least about 10%, 20%, 30%, 40%, 50%, 60%, 70%, 80%, 90%, 1-fold, 2-fold, 3-fold, 4-fold or more in comparison to an untreated cell.

As used herein, the terms "inhibit", "prevent" or "reduce," or "inhibiting", "preventing" or "reducing" are used interchangeably herein. These terms refer to the decrease in a measured parameter in a treated cell (tissue or subject) in comparison to an untreated cell (tissue or subject). A comparison can also be made of the same cell or tissue or subject between before and after treatment. In some embodiments, the decrease in the treated cell is at least about 10%, 20%, 30%, 40%, 50%, 60%, 70%, 80%, 90%, or completely inhibited in comparison to an untreated cell.

As used herein, "treatment," "treating" or "ameliorating" are used interchangeably. These terms refer to an approach for obtaining beneficial or desired results including, but not limited to, therapeutic benefit and/or a prophylactic benefit. Therapeutic benefit pertains to eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, "effective amount" means an amount sufficient to treat a subject afflicted with a disease or to alleviate a symptom or a complication associated with the disease.

As used herein, "subject" refers to either a human or non-human animal.

In one aspect, the present invention provides a method for reducing neurological damage to or risk of suffering neurological diseases in embryos or offspring, comprising administering an effective amount of an immunomodulatory protein derived from *Ganoderma*, or a recombinant or a composition thereof, to a pregnant subject exposed to particulate matter.

In another aspect, the present invention provides a method for enhancing cognition in embryos or offspring, comprising administering an effective amount of an immunomodulatory protein derived from *Ganoderma*, or a recombinant or a composition thereof, to a pregnant subject exposed to particulate matter.

In one embodiment, the method of the invention can prevent neurological damage to or neurological diseases in embryos or offspring.

In one embodiment, the neurological damage is cognitive damage. Cognition includes, but is not limited to, memory function, long-term memory, short-term memory, working memory and spatial cognition.

In one embodiment, the neurological disease is a neurodegenerative disease, schizophrenia or autism disorder. Examples of neurodegenerative diseases that can be prevented according to the invention include amyotrophic lateral sclerosis (ALS), trigeminal neuralgia, glossopharyngeal neuralgia, Bell's palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson-plus syndromes (e.g., multiple system atrophy, progressive supranuclear palsy, and corticobasal degeneration), dementia, frontotemporal dementia, demyelinating diseases (e.g., Guillain-Barre syndrome and multiple sclerosis), Charcot-Marie-Tooth disease (CMT; also known as hereditary motor and sensory neuropathy (HMSN), hereditary sensorimotor neuropathy (HSMN), and peroneal muscular atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS dementia complex (also known as HIV dementia, HIV encephalopathy, and HIV-associated dementia).

In one embodiment, the immunomodulatory protein or a recombinant thereof is derived from *Ganoderma lucidum, Ganoderma lucidum, Ganoderma tsugae, Ganoderma microsporum* or *Ganoderma sinensis.*

In one embodiment, the immunomodulatory protein of *Ganoderma* or a recombinant thereof comprises an amino acid sequence selected from the group consisting of (1) -Leu-Ala-Trp-Asn-Val-Lys-(LAWNVK; SEQ ID NO:1), (2) -Asp-Leu-Gly-Val-Arg-Pro-Ser-Tyr-Ala-Val- (DLGVRPSYAV; SEQ ID NO:2), (3) the amino acid sequence of: MSDTALIFTLAWNVKQLAFDYTPNWGR-GRPSSFIDTVTFPTVLTDKAYTY RVVVSGKDLGVRPSYAVESDGSQKINFLEYNSGY-GIADTNTIQVYVIDPD TGNNFIVAQWN (SEQ ID NO: 3) and (4) the amino acid sequence of EAEAEFMSDTA-LIFTLAWNVKQLAFDYTPNWGRGRPS SFIDTVTFPTVLT DKAY-TYRVVVSGKDLGVRPSYAVESDGSQKINFLEYNSGY-GIADTNTIQV YVIDPDTGNNFIVAQWNYLEQKLI-SEEDLNSAVDHHHHHH (SEQ ID NO: 4).

In one embodiment, the effective amount of the immunomodulatory protein ranges from about 0.01 mg/kg to about 5 mg/kg. In some embodiments, the effective amount ranges from about 0.01 mg/kg to about 4 mg/kg, about 0.01 mg/kg to about 4.5 mg/kg, about 0.01 mg/kg to about 4 mg/kg, about 0.01 mg/kg to about 3.5 mg/kg, about 0.01 mg/kg to about 3 mg/kg, about 0.01 mg/kg to about 2.5 mg/kg, about 0.01 mg/kg to about 2 mg/kg, about 0.01 mg/kg to about 1.5 mg/kg, about 0.01 mg/kg to about 1 mg/kg, about 0.01 mg/kg to about 0.5 mg/kg, about 0.05 mg/kg to about 5 mg/kg, about 0.05 mg/kg to about 4.5 mg/kg, about 0.05 mg/kg to about 4.5 mg/kg, about 0.05 mg/kg to about 4 mg/kg, about 0.05 mg/kg to about 3.5 mg/kg, about 0.05 mg/kg to about 3 mg/kg, about 0.05 mg/kg to about 2.5 mg/kg, about 0.05 mg/kg to about 2 mg/kg, about 0.05 mg/kg to about 1.5 mg/kg, about 0.05 mg/kg to about 1 mg/kg, about 0.05 mg/kg to about 0.5 mg/kg, about 0.1 mg/kg to about 5 mg/kg, about 0.1 mg/kg to about 4.5 mg/kg, about 0.1 mg/kg to about 4 mg/kg, about 0.1 mg/kg to about 3.5 mg/kg, about 0.1 mg/kg to about 3 mg/kg, about 0.1 mg/kg to about 2.5 mg/kg, about 0.1 mg/kg to about 2 mg/kg, about 0.1 mg/kg to about 1.5 mg/kg, about 0.1 mg/kg to about 1 mg/kg, about 0.1 mg/kg to about 0.5 mg/kg, about 0.5 mg/kg to about 5 mg/kg, about 1 mg/kg to about 5 mg/kg, about 1.5 mg/kg to about 5 mg/kg, about 2 mg/kg to about 5 mg/kg, about 2.5 mg/kg to about 5 mg/kg, about 3 mg/kg to about 5 mg/kg, about 3.5 mg/kg to about 5 mg/kg or about 4 mg/kg to about 5 mg/kg.

The immunomodulatory protein or a recombination thereof of the invention can be administered to a patient either alone or in pharmaceutical compositions where it is mixed with suitable carriers and excipients. The immunomodulatory protein, recombination thereof or composition of the invention can be administered parenterally, such as by intravenous injection or infusion, intraperitoneal injection, subcutaneous injection, or intramuscular injection. The immunomodulatory protein, recombination thereof or composition can be administered orally or rectally through appropriate formulation with carriers and excipients to form tablets, pills, capsules, liquids, gels, syrups, slurries, suspensions and the like. The immunomodulatory protein, recombination thereof or composition can be administered topically, such as by skin patch. The immunomodulatory protein, recombination thereof or composition can be formulated into topical creams, skin or mucosal patch, liquids or gels suitable to topical application to skin or mucosal membrane surfaces. The immunomodulatory protein, recombination thereof or composition can be administered by inhaler to the respiratory tract for local or systemic treatment of cancers.

The dosage of the immunomodulatory protein, recombination thereof or composition suitable for use according to the present invention can be determined by those skilled in the art on the basis of the disclosure herein. The medicament will contain an effective dosage (depending upon the route of administration and pharmacokinetics of the active agent) of suitable pharmaceutical carriers and excipients suitable for the particular route of administration of the formulation (i.e., oral, parenteral, topical or by inhalation). The immunomodulatory protein or a recombination thereof is mixed into the pharmaceutical composition by means of mixing, dissolving, granulating, dragee-making, emulsifying, encapsulating, entrapping or lyophilizing processes. The pharmaceutical compositions for parenteral administration include aqueous solutions of the inventive polypeptide in water-soluble form. Additionally, suspensions of the inventive polypeptide may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

In another embodiment, the immunomodulatory protein or a recombination thereof can be combined with a neurite outgrowth agent for combination therapy in promoting neurite outgrowth or treating and/or preventing a neurological disorder. The immunomodulatory protein or a recombinant thereof also can be combined with a neurite outgrowth agent as a pharmaceutical composition. That is, the invention provides a pharmaceutical composition comprising the immunomodulatory protein or a recombinant thereof and an additional neurite outgrowth agent and the composition can promote neurite outgrowth or treat and/or prevent a neurological disorder. In one embodiment, the neurite outgrowth agent is a nicotinamide adenine dinucleotide (NAD) analogue; a neurotrophic factor containing a 5-acyl-2-amino-1, 3-selenazole analogue; a neurotrophic factor containing ebselen; a neurite outgrowth agent containing at least one compound selected from the group consisting of coffeic acid and a derivative thereof; a neurite outgrowth agent containing at least one plant extract selected from the group consisting of rosemary and sage that contains carnosic acid; a cell death suppressing substance containing lysophosphatidylethanolamine; a neurite outgrowth composition containing a cell organelle alkalinization agent such as monensin or concanamycin A; a neurite outgrowth agent containing polyalkoxyflavonoid such as nobiletin or tangeretin; a neurite outgrowth activator containing a glycosaminoglycan derivative; a neurite outgrowth agent containing a lactacystin derivative; a neurite outgrowth agent containing a small molecule heterocyclic ketone or thioester compound; a neurite outgrowth agent containing derivatives of ganglioside and N-acyl-N-lyso-ganglioside, N'-acyl-N'-lyso-ganglioside, and N,N-di- or poly-acyl-N,N-dilyso-ganglioside; a neurite outgrowth agent comprising a chondroitin sulfate/dermatan sulfate hybrid chain containing a disaccharide of GlcUA(2S)-GalNAc(4S) (B unit); a neurite outgrowth inducer containing a sugar chain having a bisecting GlcNAc, a complex carbohydrate having the aforementioned sugar chain in the structure thereof, a derivative of the aforementioned sugar chain, etc.; a neurite outgrowth inducer containing, as an active ingredient, a low-molecular-weight synthetic compound; Tctex-1-related polypeptide; TAJ polypeptide; or neural cell adhesion molecule.

Without further elaboration, it is believed that one skilled in the art can utilize the present invention to its fullest extent on the basis of the preceding description. The following examples are, therefore, to be construed as merely illustrative and not a limitation of the scope of the present invention in any way.

EXAMPLES

Materials and Methods
Particle Matters and GMI
Particle matters (PM) were added to 0.01% Tween 80 and ultrasonized (60 Hz) so that the particle size of PMs was less than 2.5 μm ($PM_{2.5}$).

The immunomodulatory protein of *Ganoderma microsporum* comprising an amino acid sequence of SEQ ID NO:4 ("GMI") was used in the experiments.

Experimental Animals
Spragus-Dawley pregnant rats used in the examples were housed in laboratory animal facility with a temperature control at 18-25° C. and a humidity of 30% to 70%. For the administration of $PM_{2.5}$, the $PM_{2.5}$ at the concentrations of 0 mg/m³, 2.5 mg/m³ and 25 mg/m³ were administered to the rats by intratracheal instillation at 3, 6, 9, 12, 15 and 18 days after pregnancy. For the administration of GMI, the GMI at the concentrations of 0 μg/kg, 0.33 μg/kg and 3.3 μg/kg were orally administered to the rats in the experiments for prevention of damage from PM2.5.

Morris Water Maze (MWM) Test
The Morris water maze (MWM) is a test of spatial learning for rodents that relies on distal cues to navigate from start locations around the perimeter of an open swimming arena to locate a submerged escape platform. The water maze method was performed as described in D'Hooge, R; De Deyn, P P (August 2001), "*Applications of the Morris water maze in the study of learning and memory*". Brain Research. Brain Research Reviews 36 (1): 60-90 with modifications.

The water maze box (160 cm×70 cm×40 cm) consisted of a small pool that contained a platform to which the patients could swim. The position of the platform was dependent on one of four large abstract visual cues (each separated by 90 degrees) that were displayed on the wall of the pool. The animals were then dropped into the water maze at each of the visual cues once a day for 5 days in order to learn the location of the platform based on each cue. The intervals of the task that triggered stimulation were the start interval, or when an animal was dropped in the water maze, and the reinforcement interval, or when the animal found and rested upon the platform.

Working Memory Test
The test was performed with MWM for six days. The water maze box was the one mentioned in MWM test. The position of the platform was changed each day. The rat was trained once a day to explore the platform for one minute. After the platform was founded, the rat stayed on the platform for 20 seconds. In the test, the rat explored the platform for 60 seconds and the total time spent by the rat to explore the platform was recorded.

Novel Object and Location Recognition Test (NOR & NOL)
The novel object recognition memory test assessed the ability to recognize a novel object in the environment after a delay. The training apparatus was a clear Plexiglas box (100 cm×100 cm×50 cm). The rat was placed in the box without stress for 10 minutes for acclimation. Two objects with the same shape and color were placed in the box. For two consecutive days, the rat was placed in the box and allowed to explore the two identical objects for 5 min, and the total time spent and the frequency of exploring both objects were recorded. On the third day, the object at the right side of the box was changed to one with a different shape and color than the object on the left side of the box, and then the rat was placed in the box for 5 minutes. The total time spent and the frequency of exploring both objects were recorded.

On the fourth and fifth days, two identical objects, different from those mentioned above, were placed in the box. The rat was then placed in the box for 5 minutes and the total time spent and the frequency of exploring both objects were recorded. On the sixth day, the object on the right side of the box was changed to one with a different shape and color than the object on the left side of the box, and the rat was then placed in the box for 5 minutes. The total time spent and the frequency of exploring both objects were recorded.

Neuronal Morphology Analysis by Bonfire Program
The Bonfire program is a semi-automated approach to the analysis of dendrite and axon morphology that builds upon available open-source morphological analysis tools. The Bonfire program requires the use of two open-source analysis tools, the NeuronJ plugin to ImageJ and NeuronStudio. Neurons are traced in ImageJ, and NeuronStudio is used to define the connectivity between neurites.

Golgi Staining
Brain tissues were immersed in a mixture of A solution and B solution of FD Rapid GolgiStain Kit at a ratio of 1:1 at room temperature in the dark. After 2 to 3 weeks, the resulting brain tissues were transferred to C solution at 4° C. for 48 hrs. Sections (80 μm) were mounted onto slides coated with 0.3% gelatin in $dH_2O$. After brief drying, slides were dipped in 40% sucrose 3 times and air-dried for 72 hrs in the dark. Slides were immersed in a mixture of D solution and E solution, then transferred to a developing solution. Slides were then dehydrated through graded ethanols of 50%, 75%, 95% and 100%, immersed in Xylene, and then coverslipped using DPX mounting medium.

MicroRNA Profile Analysis
Cortex and hippocampus of fetal rat obtained from 18 days' pregnant female rats were separated and placed in TRIzol, respectively. The neurological development related disease in brain and neurologic diseases were measured using Rat Neurological Development & Disease miRNA PCR array. RNAs of the tissues were extracted and reverse transcription reactions were performed. miRNA values were obtained by QPCR.

Example 1 GMI Improves Brain Development Retardation Caused by $PM_{2.5}$

Figure 1B:
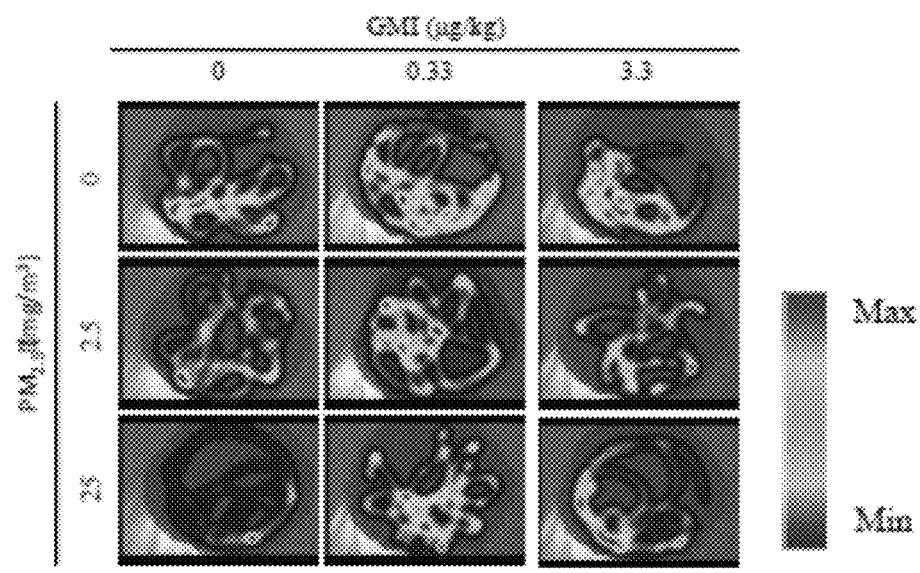

The long-term memory of the offspring of the pregnant rats that received $PM_{2.5}$ or both $PM_{2.5}$ and GMI was assayed by the MWM test. As shown in FIG. 1(a), the offspring of the pregnant rats that received high dose of $PM_{2.5}$ spent a longer time to explore the platform, while those that received both $PM_{2.5}$ and GMI took less time. The hot spots in FIG. 1(b) show that the offspring of the pregnant rats that received $PM_{2.5}$ swam around the box, whereas the offspring of the pregnant rats that received GMI had higher frequency of swimming at the quadrant with platform. The results show that GMI can enhance the long-term memory of the offspring.

Figure 2:
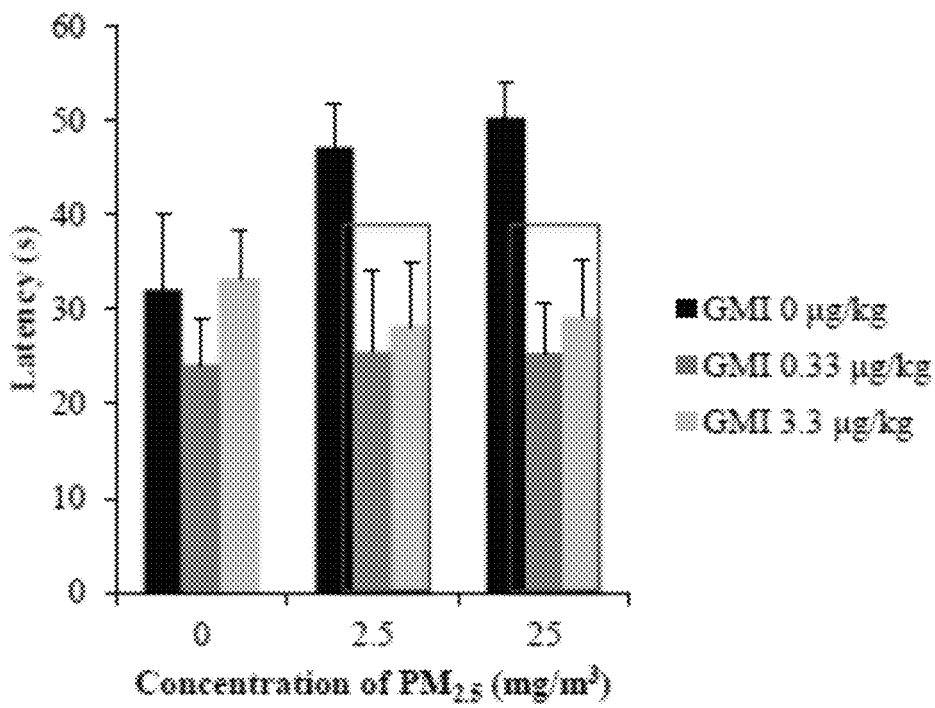
FIG. 2 shows that GMI can enhance the working memory of offspring.

The working memory of the offspring of the pregnant rats that received $PM_{2.5}$ or both $PM_{2.5}$ and GMI was assayed by the MWM test. FIG. 2 shows that offspring of the pregnant rats that received both $PM_{2.5}$ and GMI spent less time to find the platform than those that received high dose of $PM_{2.5}$. The results show that GMI can enhance the working memory of the offspring.

Figure 3:
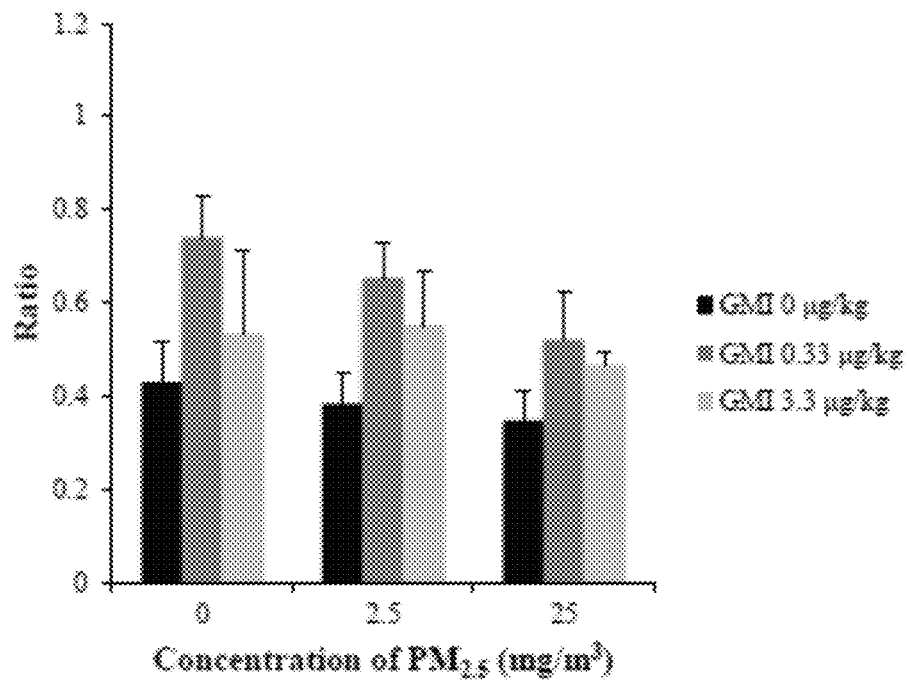
FIG. 3 shows that GMI can enhance the long-term memory of offspring.
Figure 4:
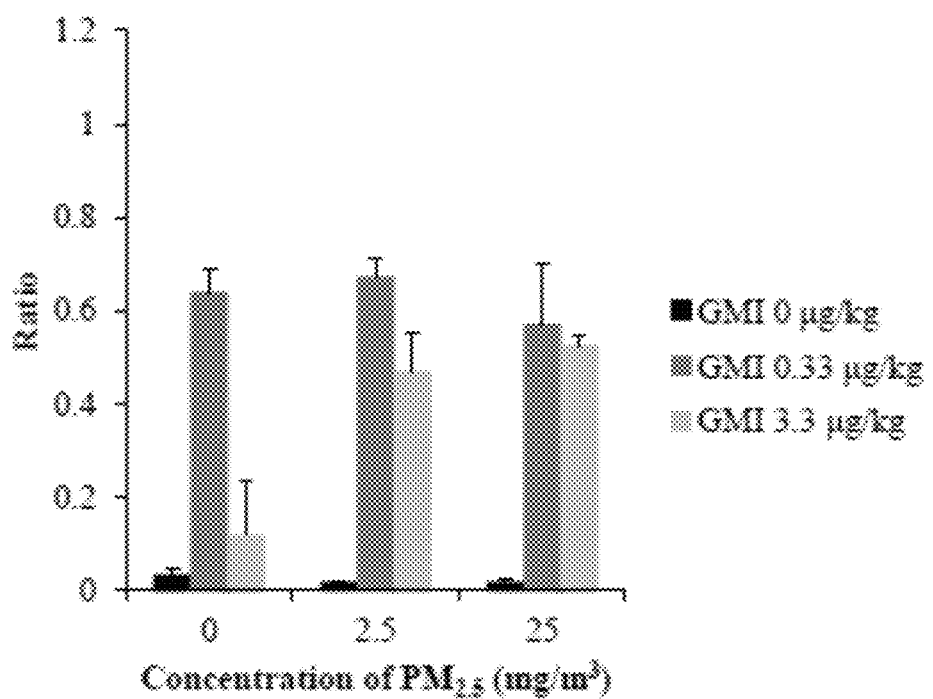
FIG. 4 shows that GMI can enhance the spatial cognition of offspring.
Figure 5A:
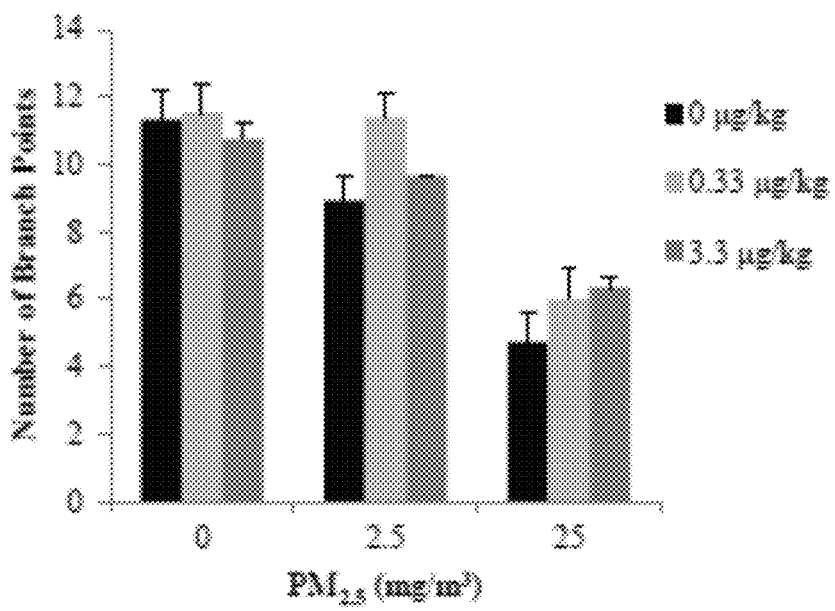
FIGS. 5 (*a*) to (*d*) show that GMI can effectively protect memory formation and reduce damage of $PM_{2.5}$ to neurites. Golgi staining was used to observe brain nerve cells to detect the complexity of dendritic branch to explore the morphology of neuron synapses and the ability of integrating signals. According to Soil analysis results, the neurites of the offsprings of the pregnant rats received both $PM_{2.5}$ and GMI have higher number of branch tips for hippocampus CA1 region (a) and for hippocampus CA3 region (c) and longer length for hippocampus CA1 region (b) and for hippocampus CA3 region (d) that those received $PM_{2.5}$ only.
Figure 5B:
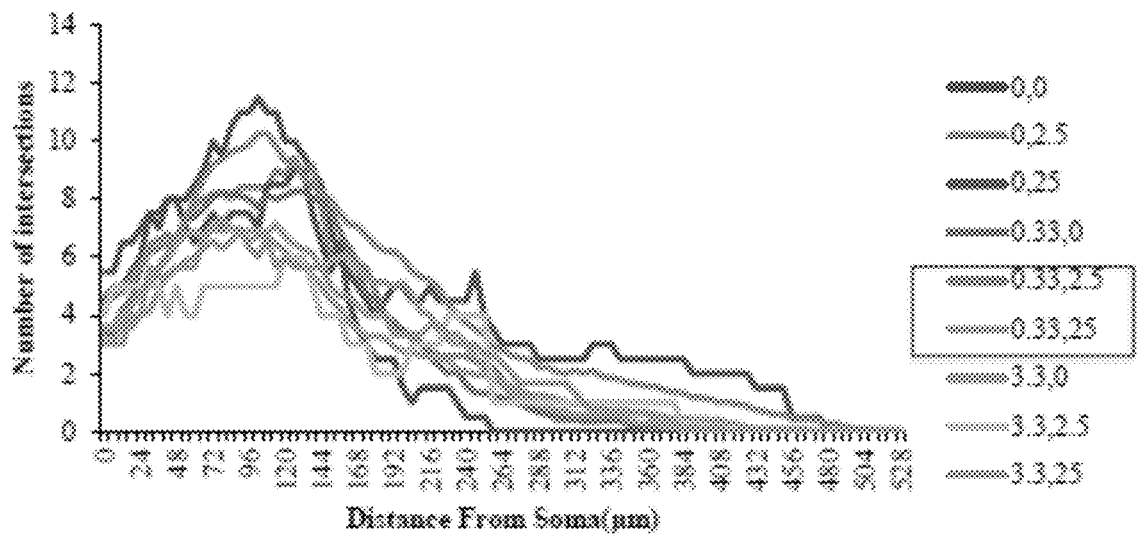
Figure 5C:
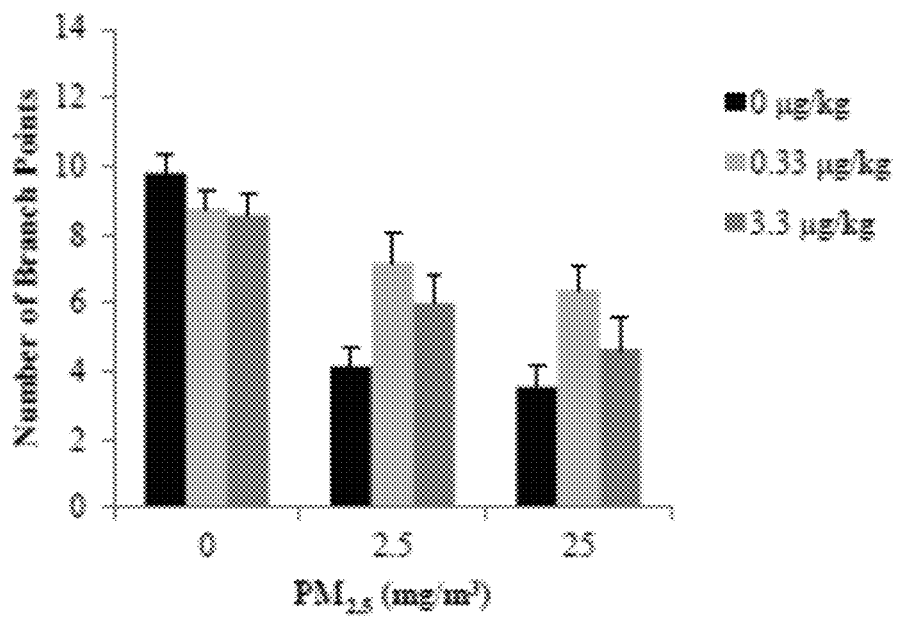
Figure 5D:
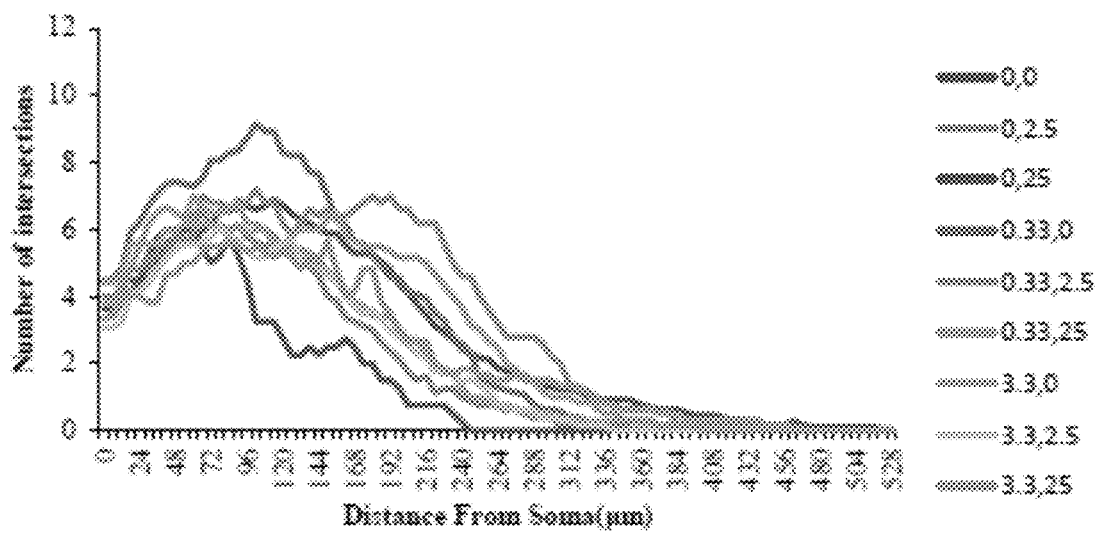

The memory capacity of the offspring of the pregnant rats that received $PM_{2.5}$ or both $PM_{2.5}$ and GMI was assayed by the NOR & NOL. As shown in FIG. 3, the offspring of the pregnant rats that received both $PM_{2.5}$ and GMI spent more time touching the new object than the offspring of the pregnant rats that received $PM_{2.5}$. The results show that GMI can enhance the long-term memory of the offspring. FIG. 4 shows that the offspring of the pregnant rats that received GMI spent more time touching the location-changed object than the offspring of the pregnant rats that received $PM_{2.5}$. The results show that GMI can enhance the spatial cognition of the offspring.

Example 2 Neuronal Morphology Analysis

The Bonfire program was used to analyze branching behaviors and dendrite extension length of hippocampus neurons. As shown in FIG. 5, the neurites of the offspring of the pregnant rats that received both $PM_{2.5}$ and GMI have a greater number of branch tips (FIG. 5(a) for hippocampus CA1 region and FIG. 5(c) for hippocampus CA3 region) and length thereof (FIG. 5(b) for hippocampus CA1 region and FIG. 5(d) for hippocampus CA3 region) than those that received $PM_{2.5}$ only. The results show that GMI can effectively protect memory formation and reduce damage from $PM_{2.5}$ on neurites.

Example 3 GMI Reduces Risk of Suffering Neurological Diseases

In comparison with the control group, the following genes of cortex and hippocampus of fetal rat obtained from 18 days' pregnant female rats that received PM2.5 were regulated according to microRNA profile analysis. The potential diseases of the regulated genes include Schizophrenia, prion diseases, autistic disorders, and Alzheimer. For the fetal rat obtained from 18 days' pregnant female rats that received both $PM_{2.5}$ and GMI, the regulated genes were recovered, so the risk of suffering neurological diseases was reduced.

| Hippocampus genes | | | |
| --- | --- | --- | --- |
| rno-miR-433-3p ↓ | | rno-miR-433-3p ↓<br>rno-miR-382-5p ↓ | Alzheimer |
| rno-miR-33-5p ↓ | rno-miR-409a-3p ↓ | | Schizophrenia |
| rno-miR-431 ↓ | | rno-miR-539-5p ↓ | Autistic Disorders |
| rno-miR-212-3p ↓ | | | |

| Cotex genes | | | | | |
| --- | --- | --- | --- | --- | --- |
| rno-miR-9a-3p ↓ | rno-miR-9a-3p ↓ | rno-miR-9a-3p ↓ | | rno-miR-9a-3p ↓ | Schizophrenia |
| rno-miR-489-3p ↓ | rno-miR-489-3p ↓ | rno-miR-489-3p ↓ | | | |
| rno-miR-33-5p ↑ | rno-miR-30d-5p ↓ | rno-miR-33-5p ↑ | | | |
| | rno-miR-346 ↓ | rno-miR-150-5p ↓ | | | |
| rno-miR-339-5p ↓ | rno-miR-339-5p ↓ | rno-miR-339-5p ↓ | | | Prion |
| | rno-miR-191a-5p ↓ | rno-miR-139-5p ↓ | | | Diseases |
| | | rno-miR-431 ↓ | | | Autistic |
| | | rno-miR-598-3p ↓ | | | Disorders |
| rno-miR-433-3p ↓ | rno-miR-433-3p ↓ | rno-miR-433-3p ↓ | | | Alzheimer |
| rno-miR-151-3p ↓ | rno-miR-151-3p ↓ | rno-miR-151-3p ↓ | | | |
| rno-miR-107-3p ↓ | rno-miR-107-3p ↓ | rno-miR-107-3p ↓ | rno-miR-132-3p ↓ | | |
| rno-miR-181a-5p ↓ | rno-miR-181a-5p ↓ | rno-miR-181a-5p ↓ | rno-let-7e-5p ↓ | | |
| rno-miR-7b-5p ↓ | rno-miR-139-5p ↓ | rno-let-7b-5p ↓ | rno-miR-30d-5p ↓ | | |
| rno-miR-346 ↓ | | rno-miR-346 ↓ | rno-miR-298-5p ↓ | | |
| rno-miR-485-5p ↓ | | rno-miR-485-5p ↓ | rno-miR-24-3p ↓ | | |
| rno-miR-488-3p ↑ | | rno-miR-382-5p ↓ | rno-miR-28-5p ↓ | | |

I claim:

1. A method for reducing neurological damage to neurites of offspring of a pregnant subject caused by exposure of the pregnant subject to particulate matter, or enhancing working memory, memory function, spatial cognition and long-term memory in offspring of a pregnant subject, comprising administering an effective amount of an immunomodulatory protein derived from *Ganoderma*, or a recombinant or a composition thereof, to the pregnant subject exposed to particulate matter, wherein the immunomodulatory protein derived from *Ganoderma*, or a recombinant or a composition thereof comprises an amino acid sequence selected from the group consisting of the amino acid sequence of:

MSDTALIFTLAWNVKQLAFDYTPNWGRGRPSSFIDTVTFPTVLTDKAYTYRVVVSGKDLGVRPSYAVESDGSQKINFLEYNSGYGIADTNTIQVYVIDPDTGNNFIVAQWN (SEQ ID NO: 3) and the amino acid sequence of EAEAEFMSDTALIFTLAWNVKQLAFDYTPNWGRGRPSSFIDTVTFPTVLTDKAYTYRVVVSGKDLGVRPSYAVESDGSQKINFLEYNSGYGIADTNTIQVYVIDPDTGNNFIVAQWNYLEQKLISEEDLNSAVDHHHHHH-(SEQ ID NO: 4).

2. The method of claim 1, wherein the neurological damage to neurites is a damage to memory function, long-term memory, short-term memory, working memory or spatial cognition.

3. The method of claim 1, wherein the immunomodulatory protein of *Ganoderma* or a recombinant thereof comprises an amino acid sequence of SEQ ID NO:4.

4. The method of claim 1, wherein the immunomodulatory protein is orally administered.

5. The method of claim 1, wherein the effective amount of the immunomodulatory protein ranges from about 0.01 mg/kg to about 5 mg/kg.

6. The method of claim 1, wherein the effective amount of the immunomodulatory protein ranges from about 0.1 mg/kg to about 3 mg/kg.

7. The method of claim 1, wherein the immunomodulatory protein is derived from *Ganoderma microsporum*.

8. A method for reducing neurological damage to neurites of offspring of a pregnant subject caused by exposure of the pregnant subject to particulate matter, or enhancing working memory, memory function, spatial cognition and long-term memory in offspring of a pregnant subject, comprising administering an effective amount of an immunomodulatory protein derived from *Ganoderma*, or a recombinant or a composition thereof, to the pregnant subject exposed to particulate matter, wherein the immunomodulatory protein derived from *Ganoderma*, or a recombinant or a composition thereof comprises an amino acid sequence selected from the group consisting of: (1) Leu-Ala-Trp-Asp-Val-Lys (LAWDVK) (SEQ ID NO: 5) and (2) Asn-Leu-Gly-Val-Lys-Pro-Ser-Tyr-Ala-Val (NLGVKPSYAV) (SEQ ID NO: 6).

* * * * *

SEQUENCE LISTING

<160> NUMBER OF SEQ ID NOS: 6

<210> SEQ ID NO 1
<211> LENGTH: 6
<212> TYPE: PRT
<213> ORGANISM: Ganoderma microsporum

<400> SEQUENCE: 1

Leu Ala Trp Asn Val Lys
1               5

<210> SEQ ID NO 2
<211> LENGTH: 10
<212> TYPE: PRT
<213> ORGANISM: Ganoderma microsporum

<400> SEQUENCE: 2

Asp Leu Gly Val Arg Pro Ser Tyr Ala Val
1               5                   10

<210> SEQ ID NO 3
<211> LENGTH: 111
<212> TYPE: PRT
<213> ORGANISM: Ganoderma microsporum

<400> SEQUENCE: 3

Met Ser Asp Thr Ala Leu Ile Phe Thr Leu Ala Trp Asn Val Lys Gln
1               5                   10                  15

Leu Ala Phe Asp Tyr Thr Pro Asn Trp Gly Arg Gly Arg Pro Ser Ser
            20                  25                  30

Phe Ile Asp Thr Val Thr Phe Pro Thr Val Leu Thr Asp Lys Ala Tyr
        35                  40                  45

Thr Tyr Arg Val Val Val Ser Gly Lys Asp Leu Gly Val Arg Pro Ser
    50                  55                  60

Tyr Ala Val Glu Ser Asp Gly Ser Gln Lys Ile Asn Phe Leu Glu Tyr
65                  70                  75                  80

Asn Ser Gly Tyr Gly Ile Ala Asp Thr Asn Thr Ile Gln Val Tyr Val
                85                  90                  95

Ile Asp Pro Asp Thr Gly Asn Asn Phe Ile Val Ala Gln Trp Asn
            100                 105                 110

<210> SEQ ID NO 4
<211> LENGTH: 140
<212> TYPE: PRT
<213> ORGANISM: Ganoderma microsporum

<400> SEQUENCE: 4

Glu Ala Glu Ala Glu Phe Met Ser Asp Thr Ala Leu Ile Phe Thr Leu
1               5                   10                  15

Ala Trp Asn Val Lys Gln Leu Ala Phe Asp Tyr Thr Pro Asn Trp Gly
            20                  25                  30

Arg Gly Arg Pro Ser Ser Phe Ile Asp Thr Val Thr Phe Pro Thr Val
        35                  40                  45

Leu Thr Asp Lys Ala Tyr Thr Tyr Arg Val Val Val Ser Gly Lys Asp
    50                  55                  60

Leu Gly Val Arg Pro Ser Tyr Ala Val Glu Ser Asp Gly Ser Gln Lys
65                  70                  75                  80

Ile Asn Phe Leu Glu Tyr Asn Ser Gly Tyr Gly Ile Ala Asp Thr Asn
                85                  90                  95

-continued

```
Thr Ile Gln Val Tyr Val Ile Asp Pro Asp Thr Gly Asn Asn Phe Ile
            100                 105                 110

Val Ala Gln Trp Asn Tyr Leu Glu Gln Lys Leu Ile Ser Glu Glu Asp
        115                 120                 125

Leu Asn Ser Ala Val Asp His His His His His
    130             135             140

<210> SEQ ID NO 5
<211> LENGTH: 6
<212> TYPE: PRT
<213> ORGANISM: Ganoderma microsporum

<400> SEQUENCE: 5

Leu Ala Trp Asp Val Lys
1               5

<210> SEQ ID NO 6
<211> LENGTH: 10
<212> TYPE: PRT
<213> ORGANISM: Ganoderma microsporum

<400> SEQUENCE: 6

Asn Leu Gly Val Lys Pro Ser Tyr Ala Val
1               5                   10
```